United States Patent [19]

Gray

[11] Patent Number: 5,413,005
[45] Date of Patent: May 9, 1995

[54] SAMPLE COLLECTOR FOR FOG-CONTAINING WASTEWATER

[75] Inventor: Keith Gray, Deerfield, Ill.

[73] Assignee: Environmental Monitoring and Technologies, Inc., Morton Grove, Ill.

[21] Appl. No.: 177,075

[22] Filed: Jan. 3, 1994

[51] Int. Cl.⁶ .............................................. G01N 1/20
[52] U.S. Cl. .............................. 73/863.43; 73/863.52
[58] Field of Search ........... 73/863.43, 863.52, 864.34, 73/863.53

[56] References Cited

U.S. PATENT DOCUMENTS

| | | | |
|---|---|---|---|
| 2,800,797 | 7/1957 | Honstead | 73/863.43 X |
| 3,929,017 | 12/1975 | Kowolski | 73/863.02 X |
| 3,962,922 | 6/1976 | Takeuchi | 73/215 X |
| 4,317,378 | 3/1982 | Mustard | 73/863.52 X |
| 4,403,517 | 9/1983 | Thomte | 73/863.43 X |
| 4,762,009 | 8/1988 | Scrudto | 73/863.52 |
| 5,009,112 | 4/1991 | Lawrence et al. | 73/863.52 X |
| 5,347,877 | 9/1994 | Gadbois | 73/863.52 |

*Primary Examiner*—Thomas P. Noland
*Attorney, Agent, or Firm*—David D. Kaufman

[57] ABSTRACT

A funnel is operationally mountable on the downstream side of a weir positioned in a wastewater stream which contains oils, fats and/or grease. The funnel has a sample port near the discharge neck and tubing is connected to the funnel in communication with the sample port. The opposite end of the tubing is connected to a pump. Wastewater flowing over the weir flows into the funnel and is agitated and mixed. Operation of the pump causes a homogeneous and representative sample to be withdrawn from the stream.

7 Claims, 1 Drawing Sheet

SAMPLE COLLECTOR FOR FOG-CONTAINING WASTEWATER

BACKGROUND OF THE INVENTION

This invention relates to wastewater pollution monitoring and, more particularly, to a device and method for manually collecting for analysis relatively representative samples of wastewater containing materials not homogeneous within the effluent, such as, fats, oils and grease (FOG).

Wastewater samples taken for analysis and pollution control are obtained by two broad categories of sampling methods. One method takes a number of partial samples over a period of time and combines them into a composite sample in the same container. Composite sampling is carried out automatically, with the sample probe submerged in the effluent stream. Under normal circumstances, the composite sample method produces water samples which are most nearly representative of the wastewater flow and thus result in more precise and accurate analysis of the concentration of pollutants.

The second sampling method entails the taking of sequential or discrete samples which are generally referred to as grab samples. In its most basic form, a grab sample is obtained by placing a container, such as a bottle, into the flow of a wastewater stream and taking the collected sample to the laboratory for analysis. A grab sample, in effect, takes a single shot or stop action picture of the effluent flow and thus is less likely to produce an approximately representative sample. Nevertheless, government regulations dictate that analysis of FOG-containing wastewater be made from grab samples for seemingly logical reasons.

Fats, oils and greases (as well as numerous volatile organic compounds) invariably tend to float on the surface of water because of their relatively lower density. The submerged probe used in automatic composite sampling is ineffective to account for such layered flow. Recommended current practice suggests that grab samples be collected by filling the sample container just below the water surface of the flow channel and also that the sample be taken near the center of the flow channel where the turbulence is at a maximum. The obvious objective of such practice is an attempt to obtain a well mixed sample which is as homogeneous and representative as possible under the circumstances. Unfortunately, grab samples obtained as described are generally heterogeneous and seldom approximate a representative sample.

While efforts have been made to provide improved liquid sampling apparatus, I am not aware that they have successfully overcome the problem of sampling FOG-containing wastewater. For example, U.S. Pat. No. 4,317,378 shows a relatively complex device including counterweights and electrical actuators and timers designed to obtain a representative flow sample and filter out solids. Although the patented device conceivably might be used for composite or grab sampling, it does not address the question of obtaining a relatively homogeneous sample containing FOG.

There thus exists a need for a sample collecting device which automatically mixes the wastewater flow so that samples obtained thereby more nearly approximate a representative sample. There is also a need for a device of the character described which is portable and simple to use so that it may be applied as often and wherever required.

BRIEF SUMMARY OF THE INVENTION

The present invention provides a method and device for taking samples of FOG-containing wastewater which insure that the sample is well mixed and is approximately representative of the FOG concentration of the effluent. The invention is handy, portable and simple to use wherever desired.

It is well known that most systems for monitoring the rate of flow of a wastewater stream involve the use of a dam or weir positioned in or across the stream. The weir may be permanently positioned in the flow channel or it may be temporarily inserted while tests are being run, but its presence is required to raise the level of the flow thereabove to permit flow rate measurement in well known ways. The present invention cooperates with and makes use of the weir to produce more representative samples of FOG-containing wastewater.

Briefly, the invention comprises a funnel-shaped collector having the customary reduced neck opening at the bottom thereof. The collector is also provided with a sample inlet port adjacent the bottom thereof and an extension to which is connectable a sample conduit such as conventional tubing. Adjustable hanger members are connected to the collector and said hanger members are adapted to support the collector from a weir plate or the like. The collector is positionable in front of and/or beneath the cutout of the weir so that the flow passing through the cutout passes into the collector before joining the stream therebeneath.

The funnel shape of the collector causes automatic mixing and agitation of the stream flowing thereinto. The free end of the sample conduit is connectable to suitable pump means, such as a conventional peristaltic pump. When a sample is desired, it is simply necessary to operate the pump and thereby draw a well mixed and approximately representative sample into a container for laboratory analysis.

The invention is extremely simple to use and is adjustable to accommodate any weir or supporting surface. The invention thus may be moved from place to place and used wherever desired.

Numerous other advantages and features of the present invention will become apparent from the following detailed description Of the invention, from the claims and from the accompanying drawings.

BRIEF DESCRIPTION OF THE DRAWINGS

In the accompanying drawings forming a part of the specification, and in which like numerals are employed to designate like parts throughout.

DETAILED DESCRIPTION OF THE INVENTION

Figure 1:
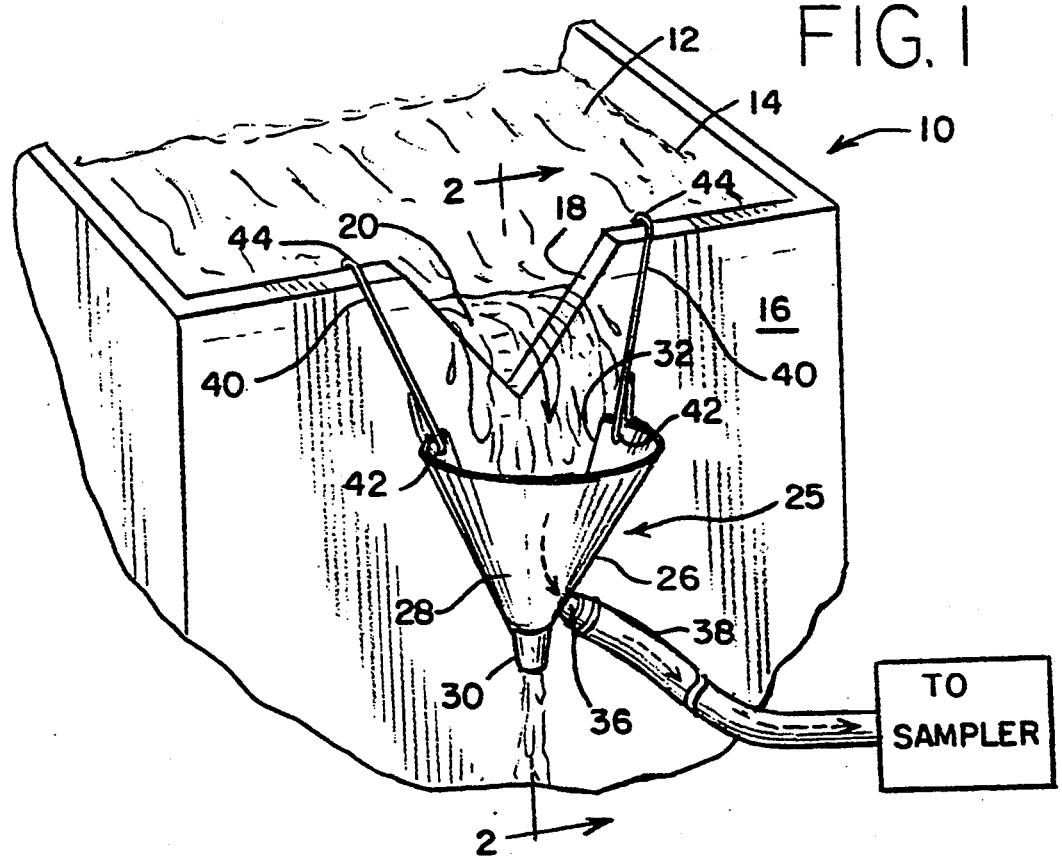
FIG. 1 is a fragmentary perspective view of a wastewater flow channel showing operationally mounted thereon a collector embodying the principles of the invention.
Figure 2:
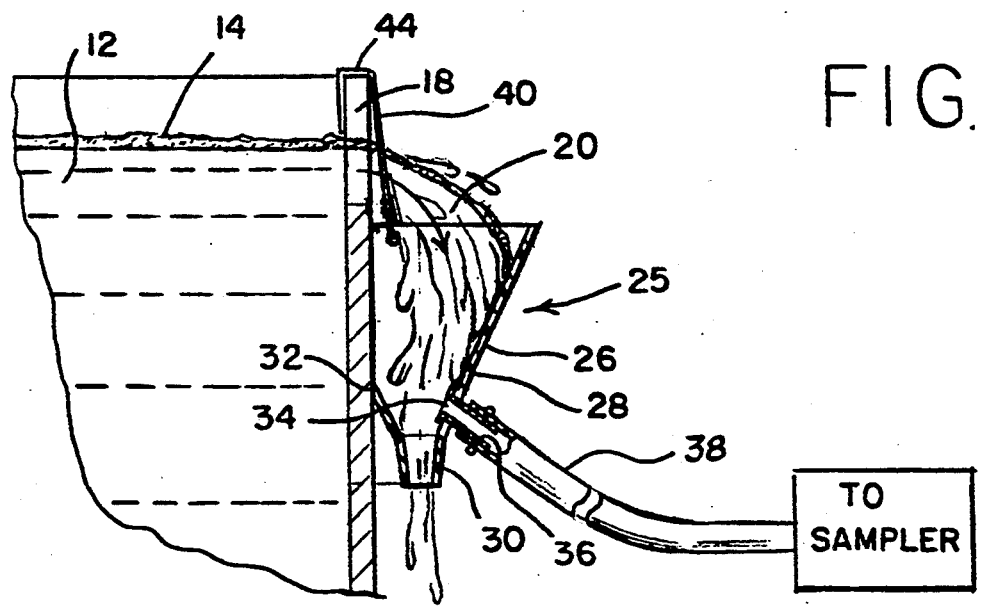
FIG. 2 is a vertical sectional view on the plane of line 2—2 of FIG. 1.

Referring in greater detail to the drawings, the reference numeral 10 indicates a channel carrying a stream of wastewater 12, said wastewater being contaminated with a layer of FOG 14 floating on the top thereof. A dam or weir 16 is operationally positioned in the channel 10 and said weir is provided with a central opening 18 which may be V-shaped as illustrated. The weir opening 18 directs a centralized stream or waterfall 20 to flow therethrough.

A collector embodying the principles of the invention is identified generally by the numeral 25. Collector 25 comprises a funnel-shaped member 26 having an inverted conic body 28 which tapers downwardly to a relatively small diameter discharge neck or hole 30. A section of the conic body 28 is cut out to provide a straight edge 32, said edge preferably defining a hyperbolic curve.

The conic body 28 is formed with a sample port 34 above and in close proximity to the discharge neck 30. A cylindrical extension or nipple 36 projects from the body 28 and affords a means for connection thereto of a sample conduit such as tubing 38.

Hanger members 40, 40 are connected to the conic body 28 adjacent opposite ends of the hyperbolic edge 32, such as through holes 42, 42 formed in said body. The hangers 40 include top hook segments 44 and preferably are adjustable, both in length and hook form, to accommodate connection to various vertical supporting surfaces such as weirs.

In use, the collector 25 is suspended from a weir 16 or the like positioned beneath the central opening 18 and with the edge 32 lying substantially flush against the weir. Waterfall 20 flowing through the opening 18 thereby flows through the collector before exiting to rejoin the main flow stream therebelow. The conic shape of the collector causes significant agitation and mixing of the FOG and water so that the exiting stream is relatively homogeneous and representative of the FOG concentration. The opposite or free end of the tubing 38 is operationally connected to a known sample device (such as ISCO Model 2900) which typically includes a peristaltic pump or the like. When a grab sample is desired, the pump is operated to cause flow through the tubing 38 and into a suitable sample container for laboratory analysis.

The grab sample obtained by the invention is automatically agitated and more nearly representative of the wastewater flow so that accurate measurements of the FOG concentration can be made. Representative composite samples are also obtainable when desired by repeated pumping and withdrawing into the same container.

From the foregoing, it should be apparent that the invention provides a simple and economical device and method for taking more representative samples of FOG-containing wastewater. It should be appreciated that a preferred embodiment of the invention has been described herein for illustrative purposes only and is not otherwise limiting of the structural and method concepts of the invention. Thus, for example, the collector 25 could also comprise an inverted pyramidal form and function in similar manner. Accordingly, changes and variations may be made by those skilled in the art without departing from the spirit and scope of the invention as defined in the appended claims.

What is claimed is:

1. A wastewater liquid sampling device comprising:
    a funnel having a wide mouth and a smaller discharge hole;
    a sample port in the wall of the funnel above said discharge hole;
    a sample withdrawing conduit connected to said funnel in communication with said sample port; and
    hangers projecting upwardly from said funnel and adapted to operationally mount said funnel from a weir so that wastewater flowing thereover flows into said funnel and is agitated before exiting through said discharge hole or sample port.

2. A liquid sampling device according to claim 1 wherein said funnel comprises a cone.

3. A liquid sampling device according to claim 2 wherein said cone comprises a section cut therefrom providing a hyperbolic curve straight edge, said straight edge adapted to abut the weir when operationally mounted thereon.

4. A liquid sampling device according to claim 1 wherein said conduit comprises a tube releasably connected to said funnel.

5. In combination with a weir operationally positioned in a wastewater stream, a sample collector comprising:
    a funnel having a wide mouth and a smaller discharge hole;
    a sample port in the wall of the funnel above said discharge hole;
    a sample withdrawing tube connected to said funnel in communication with said sample port, the free end of said tube being connectable to pump means for causing liquid to flow therethrough; and
    a pair of hanger members connected to said funnel and operationally mounting said funnel on the weir so that wastewater flowing thereover flows into said funnel and is agitated before exiting through said discharge hole or sample port.

6. The combination of claim 5 wherein said funnel comprises a cone having a section cut therefrom forming a parabolic curve straight edge, said straight edge lying substantially flush against said weir.

7. The combination of claim 6 wherein said weir comprises a central cutout and said funnel is operationally positioned directly beneath said cutout.

* * * * *